US009125943B2

(12) United States Patent
Vucica et al.

(10) Patent No.: US 9,125,943 B2
(45) Date of Patent: Sep. 8, 2015

(54) RECONSTITUTED HDL FORMULATION

(71) Applicant: CSL Limited, Parkville, Victoria (AU)

(72) Inventors: Yvonne Vucica, Bern (CH); Gary Lee Warren, Bourbonnais, IL (US)

(73) Assignee: CSL LIMITED, Parkville, Victoria (AU)

( * ) Notice: Subject to any disclaimer, the term of this patent is extended or adjusted under 35 U.S.C. 154(b) by 0 days.

(21) Appl. No.: 13/803,863

(22) Filed: Mar. 14, 2013

(65) Prior Publication Data

US 2014/0221272 A1  Aug. 7, 2014

Related U.S. Application Data

(60) Provisional application No. 61/721,771, filed on Nov. 2, 2012.

(30) Foreign Application Priority Data

Feb. 4, 2013 (EP) .................................... 13153903

(51) Int. Cl.
*A61K 47/26* (2006.01)
*A61K 47/10* (2006.01)
*A61K 47/18* (2006.01)
*C07K 14/775* (2006.01)

(52) U.S. Cl.
CPC .................. *A61K 47/26* (2013.01); *A61K 47/10* (2013.01); *A61K 47/183* (2013.01); *C07K 14/775* (2013.01)

(58) Field of Classification Search
CPC ............ A61K 38/1709; A61K 9/1275; A61K 31/685; A61K 9/0019; A61K 45/06; A61K 31/56; A61K 2300/00; A61K 47/10; A61K 47/183; A61K 47/26; C07K 14/775
See application file for complete search history.

(56) References Cited

U.S. PATENT DOCUMENTS

| 5,089,602 | A | * | 2/1992 | Isliker et al. ................. 530/359 |
| 5,652,339 | A | | 7/1997 | Lerch et al. |
| 2003/0109442 | A1 | | 6/2003 | Bisgaier et al. |
| 2004/0038891 | A1 | | 2/2004 | Bisgaier et al. |
| 2005/0142180 | A1 | | 6/2005 | Bisgaier et al. |

FOREIGN PATENT DOCUMENTS

| EP | 0 663 407 A1 | 7/1995 |
| KR | 10-2008-0062328 A | 7/2008 |
| WO | WO 2007098122 A2 * | 8/2007 |
| WO | WO 2010/057203 A2 | 5/2010 |
| WO | WO 2012000048 A1 * | 1/2012 ............ A61K 31/56 |
| WO | WO 2012/109162 A1 | 8/2012 |

OTHER PUBLICATIONS

Kim et al., "Manufacturing and Shelf Stability of Reconstituted High-density Lipoprotein for Infusion Therapy," Biotechnology and Bioprocess Engineering, vol. 16, pp. 785-792, 2011.
Wang, "Lyophilization and development of solid protein pharmaceuticals," International Journal of Pharmceutics, vol. 203, pp. 1-60, 2000.
U.S. Appl. No. 13/805,488, filed Mar. 18, 2013, Wright et al.
European Search Report issued on Jul. 19, 2013 in application No. EP 13 15 3903.
Lerch et al., "Production and Characterization of a Reconsitituted High Density Lipoprotein for Therapeutic Applications," Vox Sang, vol. 71, pp. 155-164, Sep. 1996.
International Search Report issued in application No. PCT/AU2013/001260 on Jan. 17, 2014.
International Search Report issued on Aug. 25, 2014 in application No. PCT/AU2014/000584.
Lerch et al., "Isolation and Properties of Apolipoprotein A for Therapeutic Use," Protides of Biological Fluids, vol. 36, pp. 409-416, 1989.

* cited by examiner

*Primary Examiner* — James H Alstrum Acevedo
*Assistant Examiner* — Erinne Dabkowski
(74) *Attorney, Agent, or Firm* — Foley & Lardner LLP

(57) ABSTRACT

The present invention relates to reconstituted high density lipoprotein (rHDL) formulations comprising an apolipoprotein, a lipid and a lyophilization stabilizer. Said formulations have reduced renal toxicity and good long-term stability, especially in lyophilized form.

25 Claims, 13 Drawing Sheets

——— 7.5% Sucrose
- - - - - - 1% Sucrose / 2.2% Proline
— — — - 3% Sucrose/ 1.5% Proline
—·—·—·— 4% Sucrose/ 1.2% Proline

RECONSTITUTED HDL FORMULATION

TECHNICAL FIELD

The present invention relates to reconstituted high density lipoprotein formulations, and in particular to formulations with suitable stability and biological properties for pharmaceutical use.

BACKGROUND ART

High-density lipoproteins (HDLs) form a range of lipoprotein particles found in normal serum. Mature HDL particles are present in the form of a globular structure containing proteins and lipids. Within the outer layer of these particles are the more polar lipids, phospholipids and free cholesterol, all having charged groups orientated outwards, towards the aqueous environment. The more hydrophobic lipids, such as esterified cholesterol and triglycerides, reside in the core of the particle. Newly formed or nascent HDL particles lack the lipid and are discoidal in shape. Protein components are embedded in the outer layer. The main protein component is apolipoprotein A-I (Apo A-I) with smaller amounts of Apo A-II, Apo A-IV, Apo CIII, Apo D, Apo E and Apo J. Various other proteins reside on the HDL particle, such as lecithin-cholesterol acetyl transferase, PAF acetylhydrolase and paraoxonase. HDLs are characterized by high density (>1.063 g/ml) and small size (Stoke's diameter=5 to 17 nm).

Efforts have been made to develop artificial HDLs that can be infused into the bloodstream of patients to mimic the biological effects of naturally-occurring HDLs. These artificial particles are generally referred to as "reconstituted HDL" (rHDL), or sometimes as HDL mimetics or synthetic HDL particles. The artificial particles contain components of the natural particles, in particular Apo A-I and lipids. For example, WO 2012/000048 describes rHDL comprising Apo A-I, phosphatidylcholine (PC) and a small amount of sodium cholate. WO 2012/109162 describes rHDL comprising Apo A-I, sphingomyelin (SM) and phosphatidylglycerol (e.g. 1,2-dipalmitoyl-sn-glycero-3-[phospho-rac-(1-glycerol)] (DPPG)).

It is convenient for rHDL formulations to be lyophilized (freeze-dried) before use. Lyophilization is a commonly used method for preparing solid protein pharmaceuticals. However, this process generates a variety of freezing and drying stresses, such as concentration of the solubilized protein, formation of ice crystals, pH changes, etc. All of these stresses can denature proteins to various degrees. Thus, stabilizers are often required in a protein formulation to protect protein stability both during freezing and drying processes. In order to maintain the stability of rHDL formulations during lyophilization, stabilizers like sugars and sugar alcohols have been used. For example, U.S. Pat. No. 5,089,602 discloses plasma-derived lipoproteins that are stabilized with 10% sucrose or a mixture of 10% sucrose and 5% mannitol. WO 2012/000048 discloses sugar and sugar alcohol stabilizers used at a concentration from about 65 to 85 g/L of rHDL formulation (equivalent to about 6.5 to 8.5% w/w). WO 2012/109162 discloses sucrose and mannitol as stabilizers, used in a mixture at 4% w/w and 2% w/w respectively. An investigation into the manufacturing and shelf stability of rHDL was carried out in Kim et al, Biotechnology and Bioprocess Engineering 16, 785-792 (2011). Here, rHDL with an Apo A-I: soybean PC ratio of 1:150 could not be sufficiently stabilized with 1 or 5% sucrose, whereas 10% sucrose was described as optimal.

The rHDL formulations of these documents are intended for infusion therapy, but high sugar concentrations in infusion products may cause or exacerbate renal problems. This is a particular problem in the target patient population for rHDL, because these patients are often renally impaired.

Therefore, an object of the present invention was to provide alternative or improved rHDL formulations compared to these previous formulations. In particular, the inventors sought stable rHDL formulations with reduced renal toxicity.

This problem is solved by the formulation according to claim 1. Further preferred embodiments are defined in the dependent claims.

Surprisingly, it has been found that the rHDL formulation of claim 1 shows good long-term stability. By containing less lyophilization stabilizer than previous formulations, the formulation also presents less risk of renal toxicity. The low lyophilization stabilizer concentration may also allow the rHDL to perform better in functional assays of rHDL function. The inventors have also found that amino acids, particularly proline, are useful lyophilization stabilizers for rHDL formulations.

SUMMARY OF THE INVENTION

The invention provides an rHDL formulation comprising an apolipoprotein, a lipid and a lyophilization stabilizer, wherein the ratio between the apolipoprotein and the lipid is from about 1:20 to about 1:120 (mol:mol).

Preferably, the lyophilization stabilizer is present in a concentration from about 1.0% to about 6.0% (w/w of rHDL formulation), e.g. from 1.0, 1.1, 1.2 or 1.3 to 5.5, 5.6, 5.7, 5.8, 5.9, or 6.0. This low amount of lyophilization stabilizer may reduce the risk of renal toxicity. It is also particularly suitable for patients receiving contrast agents during acute coronary syndrome therapy (ACS), since these agents may compete with lyophilization stabilizer for clearance in the kidneys. In a preferred embodiment, the lyophilization stabilizer is present in a concentration from about 1.0% to less than 6.0% e.g. from about 1.0% to 5.9%. Preferably the lyophilization stabilizer is present in a concentration from about 3.0 to less than 6.0%, e.g. from about 3.0 to 5.9%. More preferably, the lyophilization stabilizer is present in a concentration from about 4.0 to 5.5%, particularly 4.3 to 5.3%, more particularly 4.3 to 5.0%, and most preferably 4.6 to 4.8% (w/w). Such formulations show good stability and low renal toxicity.

Alternatively, or in addition, it is preferred for the ratio between the apolipoprotein and the lyophilization stabilizer to be from about 1:1 to about 1:3 (w:w). In particular, the ratio between the apolipoprotein and the lyophilization stabilizer is from about 1:1 to about 1:2.4 (w:w), e.g. less than 1:2 (w:w). The inventors have found that these formulations remain stable showing few or no changes in the size distribution of lyophilized samples, even after storage for several months. However, in some embodiments, the ratio between the apolipoprotein and the lyophilization stabilizer may be less than this, e.g. from about 1:1 to about 1:7, and in particular from about 1:1 to about 1:5 (w:w).

The invention also provides an rHDL formulation comprising an apolipoprotein, a lipid and a lyophilization stabilizer, wherein the lyophilization stabilizer comprises an amino acid. Preferably the amino acid is proline. The inventors have found that amino acids are good lyophilization stabilizers for rHDL formulations, particularly when in a mixture with low amounts of other stabilizers.

DETAILED DESCRIPTION OF THE INVENTION

Within the context of the present invention, the term "reconstituted HDL (rHDL) formulation" means any artificially-produced lipoprotein formulation or composition that is functionally similar to, analogous to, corresponds to, or mimics, high density lipoprotein (HDL), typically present in blood plasma. rHDL formulations include within their scope "HDL mimetics" and "synthetic HDL particles".

Within the context of the present invention, the term "lyophilization stabilizer" means a substance that stabilizes protein during lyophilization. Such lyophilization stabilizers are well known in the art and are reviewed in, for example, Wang (2000) International Journal of Pharmaceuticals 203:1-60. A preferred lyophilization stabilizer for use in the invention comprises a sugar, a sugar alcohol, an amino acid, or a mixture thereof. For example, the inventors have found that disaccharides such as sucrose are particularly suitable sugars for use as the lyophilization stabilizer. Other disaccharides that may be used include fructose, trehalose, maltose and lactose. In addition to disaccharides, trisaccharides like raffinose and maltotriose may be used. Larger oligosaccharides may also be suitable, e.g. maltopentaose, maltohexaose and maltoheptaose. Alternatively, monosaccharides like glucose, mannose and galactose may be used. These mono-, di-, tri- and larger oligo-saccharides may be used either alone or in combination with each other. As noted above, lyophilization stabilizers that are sugar alcohols may also be used. These sugar alcohols may also be used either alone or in combination. A particular sugar alcohol for use in the invention is mannitol. Other sugar alcohols that may be used include inositol, xylitol, galactitol, and sorbitol. Other polyols like glycerol may also be suitable. Amino acids that may be used as lyophilization stabilizers include proline, glycine, serine, alanine, and lysine. Modified amino acids may also be used, for example 4-hydroxyproline, L-serine, sodium glutamate, sarcosine, and γ-aminobutyric acid. The inventors have found that proline is a particularly suitable amino acid for use as a lyophilization stabilizer.

In particular embodiments, the lyophilization stabilizer comprises a mixture of a sugar and a sugar alcohol. For example, a mixture of sucrose and mannitol may be used. The sugar and the sugar alcohol may be mixed in any suitable ratio, e.g. from about 1:1 (w:w) to about 3:1 (w:w), and in particular about 2:1 (w:w). Ratios less than 2:1 are particularly envisaged, e.g. less than 3:2. Typically, the ratio is greater than 1:5, e.g. greater than 1:2 (w:w). In some embodiments the formulation comprises less than 4% sucrose and 2% mannitol (w/w of rHDL formulation), for example 3% sucrose and 2% mannitol. In some embodiments the formulation comprises 4% sucrose and less than 2% mannitol. In some embodiments the formulation comprises less than 4% sucrose and less than 2% mannitol e.g. about 1.0% to 3.9% sucrose and about 1.0% to 1.9% (w/w) mannitol.

In particular embodiments, the lyophilization stabilizer comprises a mixture of a sugar and an amino acid. For example, a mixture of sucrose and proline may be used. The sugar and the amino acid may be mixed in any suitable ratio, e.g. from about 1:1 to about 3:1 (w:w), and in particular about 2:1 (w:w). Ratios less than 2:1 are particularly envisaged, e.g. less than 3:2 (w:w). Typically, the ratio is greater than 1:5, e.g. greater than 1:2 (w:w). Preferably the amino acid is present in a concentration of from about 1.0 to about 2.5% e.g. from 1.0, 1.2, or 1.3 to 2.0, 2.1, 2.2, 2.3, 2.4, or 2.5% (w/w of rHDL formulation). In some embodiments the formulation comprises 1.0% sucrose and 2.2% proline, or 3.0% sucrose and 1.5% proline, or 4% sucrose and 1.2% proline. The amino acid may be added to the sugar to maintain an isotonic solution. Solutions with an osmolality of greater than 350 mosmol/kg are typically hypertonic, while those of less than 250 mosmol/kg are typically hypotonic. Solutions with an osmolality of from 250 mosmol/kg to 350 mosmol/kg are typically isotonic.

In particular embodiments, the lyophilization stabilizer comprises a mixture of a sugar alcohol and an amino acid. The lyophilization stabilizer may comprise a mixture of a sugar, a sugar alcohol, and an amino acid.

The apolipoprotein may be any apolipoprotein which is a functional, biologically active component of naturally-occurring HDL or of a reconstituted high density lipoprotein/rHDL. Typically, the apolipoprotein is either a plasma-derived or recombinant apolipoprotein such as Apo A-I, Apo A-II, Apo A-V, pro-Apo A-I or a variant such as Apo A-I Milano. Preferably, the apolipoprotein is Apo A-I. More preferably the Apo A-I is either recombinantly derived comprising a wild type sequence or the Milano sequence or alternatively it is purified from human plasma. The apolipoprotein may be in the form of a biologically-active fragment of apolipoprotein. Such fragments may be naturally-occurring, chemically synthesized or recombinant. By way of example only, a biologically-active fragment of Apo A-I preferably has at least 50%, 60%, 70%, 80%, 90% or 95% to 100% or even greater than 100% of the lecithin-cholesterol acyltransferase (LCAT) stimulatory activity of Apo A-I.

In the present invention the molar ratio of apolipoprotein: lipid is typically from about 1:20 to about 1:120, and preferably from about 1:20 to about 1:100, more preferably from about 1:20 to about 1:75 (mol:mol), and in particular from 1:45 to 1:65. This range includes molar ratios such as about 1:25, 1:30, 1:35, 1:40, 1:45, 1:50, 1:55, 1:60, 1:65, 1:70, 1:75, 1:80, 1:85, 1:90, 1:95 and 1:100. A particularly advantageous ratio of apolipoprotein:lipid is from 1:40 to 1:65 (mol:mol). This ensures that the rHDL formulation according to the present invention comprises a lipid at a level which does not cause liver toxicity.

In other embodiments, the molar ratio of apolipoprotein: lipid may be in a range from about 1:80 to about 1:120. For example, the ratio may be from 1:100 to 1:115, or from 1:105 to 1:110. In these embodiments, the molar ratio may be for example from 1:80 to 1:90, from 1:90 to 1:100, or from 1:100 to 1:110. In a preferred embodiment the rHDL formulation according to the present invention comprises additionally a detergent in order to further stabilize the rHDL particles. The detergent may be any ionic (e.g. cationic, anionic, zwitterionic) detergent or non-ionic detergent, inclusive of bile acids and salts thereof, suitable for use in rHDL formulations. Ionic detergents may include bile acids and salts thereof, polysorbates (e.g. PS80), 3-[(3-Cholamidopropyl)dimethylammonio]-1-propane-sulfonate-(CHAPS), 3-[(3-Cholamidopropyl)dimethylammonio]-2-hydroxy-1-propanesulfonate (CHAPSO), cetyl trimethyl-ammonium bromide, lauroylsarcosine, tert-octyl phenyl propanesulfonic acid and 4'-amino-7-benzamido-taurocholic acid.

Bile acids are typically dihydroxylated or trihydroxylated steroids with 24 carbons, including cholic acid, deoxycholic acid, chenodeoxycholic acid or ursodeoxycholic acid. Preferably, the detergent is a bile salt such as a cholate, deoxycholate, chenodeoxycholate or ursodeoxycholate salt. A particularly preferred detergent is sodium cholate. The concentration of the detergent, in particular of sodium cholate, is preferably 0.5 to 1.5 mg/mL.

The ratio between the apolipoprotein and the lyophilization stabilizer is usually adjusted so this ratio is from about 1:1 to about 1:7 (w:w). More preferably, the ratio is from about 1:1 to about 1:3, in particular about 1:1:1 to about 1:2. In specific embodiments the rHDL formulations thus have ratios of 1:1.1, 1:1.2, 1:1.3, 1:1.4, 1:1.5, 1:1.6, 1:1.7, 1:1.8, 1:1.9 or 1:2 (w:w). It is however contemplated that for particular embodiments where there are low amounts of protein (e.g. <20 mg/mL) that the ratio between the apolipoprotein and the lyophilization stabilizer can be extended to as much as about 1:7 (w:w), e.g. about 1:4.5 (w:w).

Suitably, the apolipoprotein is at a concentration from about 5 to about 50 mg/ml. This includes 5, 8, 10, 15, 20, 25, 30, 35, 40, 45 and 50 mg/ml and any ranges between these amounts. The apolipoprotein is, preferably, at a concentration from about 25 to 45 mg/ml. In other embodiments, the apolipoprotein may be at a concentration of from about 5 to 20 mg/ml, e.g. about 8 to 12 mg/ml.

The lipid may be any lipid which is a functional, biologically active component of naturally occurring HDL or of reconstituted high density lipoprotein (rHDL). Such lipids include phospholipids, cholesterol, cholesterol-esters, fatty acids and/or triglycerides. Preferably, the lipid is at least one charged or non-charged phospholipid or a mixture thereof.

In a preferred embodiment the rHDL formulation according to the present invention comprises a combination of a detergent and a non-charged phospholipid. In an alternative preferred embodiment the rHDL formulation comprises a charged phospholipid but no detergent at all. In a further preferred embodiment the rHDL formulation comprises charged and non-charged lipids as well as a detergent.

As used herein, "non-charged phospholipids", also called neutral phospholipids, are phospholipids that have a net charge of about zero at physiological pH. Non-charged phospholipids may be zwitterions, although other types of net neutral phospholipids are known and may be used. "Charged phospholipids" are phospholipids that have a net charge at physiological pH. The charged phospholipid may comprise a single type of charged phospholipid, or a mixture of two or more different, typically like-charged phospholipids. In some examples, the charged phospholipids are negatively charged glycophospholipids.

The formulation according to the present invention may also comprise a mixture of different lipids, such as a mixture of several non-charged lipids or of a non-charged lipid and a charged lipid. Examples of phospholipids include phosphatidylcholine (lecithin), phosphatidic acid, phosphatidylethanolamine (cephalin), phosphatidylglycerol (PG), phosphatidylserine (PS), phosphatidylinositol (PI) and sphingomyelin (SM) or natural or synthetic derivatives thereof. Natural derivatives include egg phosphatidylcholine, egg phosphatidylglycerol, soy bean phosphatidylcholine, hydrogenated soy bean phosphatidylcholine, soy bean phosphatidylglycerol, brain phosphatidylserine, sphingolipids, brain sphingomyelin, egg sphingomyelin, galactocerebroside, gangliosides, cerebrosides, cephalin, cardiolipin and dicetylphospate. Synthetic derivatives include dipalmitoylphosphatidylcholine (DPPC), didecanoyl-phosphatidylcholine (DDPC), dierucoylphosphatidylcholine (DEPC), dimyristoylphosphatidylcholine (DLPC), palmitoyl-oleoylphosphatidylcholine (PMPC), palmitoylstearoyl-phosphatidylcholine (PSPC), dioleoylphosphatidyl-ethanolamine (DOPE), dilauroylphosphatidylglycerol (DLPG), distearoylphosphatidylglycerol (DSPC), dioleoyl-phosphatidylglycerol (DOPG), palmitoyloleoylphosphatidyl-glycerol (POPG), dimyrstolyphosphatidic acid (DMPA), dipalmitoylphosphatidic acid (DPPA), distearoyl-phosphatidic acid (DSPA), dipalmitoylphosphatidylserine (DPPS), distearoylphosphatidylethanolamine (DSPE), di-oleoylphosphatidylethanolamine (DOPE), dioleoyl-phosphatidylserine (DOPS), dipalmitoylsphingomyelin (DPSM) and distearoylsphingomyelin (DSSM). The phospholipid can also be a derivative or analogue of any of the above phospholipids. Best results could be obtained with phosphatidylcholine. In another embodiment the lipids in the formulation according to the present invention are sphingomyelin and a negatively charged phospholipid, such as phosphatidylglycerol (e.g. DPPG). A mixture of sphingomyelin and phosphatidylglycerol (particularly DPPG) is specifically envisaged for use in the invention. In these embodiments, the sphingomyelin and the phosphatidylglycerol may be present in any suitable ratio, e.g. from 90:10 to 99:1 (w:w), typically 95:5 to 98:2 and most typically 97:3.

The formulation according to the present invention typically has a lyophilization stabilizer concentration from about 1.0% to about 6.0% e.g. from 1.0, 1.1, 1.2 or 1.3% to 5.5, 5.6, 5.7, 5.8, 5.9, or 6.0%, preferably from about 1.0% to less than 6.0%, e.g. from about 1.0% to 5.9% (w/w of rHDL formulation). Preferably from about 3.0% to less than 6.0%, e.g. from about 3.0% to 5.9%, preferably from about 4.0 to 5.9%, preferably, from about 4.0% to 5.5%, preferably 4.3 to 5.3%, preferably 4.3 to 5.0%, and most preferably from 4.6 to 4.8% (w/w) and in said formulation the ratio between the apolipoprotein and the lipid is preferably from about 1:20 to about 1:75, more preferably from about 1:45 to about 1:65 (mol: mol). The lyophilization stabilizer is preferably a sugar (e.g. sucrose), optionally in combination with a sugar alcohol such as mannitol or sorbitol, or an amino acid such as proline.

In a preferred embodiment, the rHDL formulation according to the present invention has a pH in the range of 6 to 8, preferably within the range of 7 to 8. Even more preferably the pH is in the range of 7.3 to 7.7.

In a preferred embodiment of the present invention, the formulation is lyophilized. Due to the presence of lyophilization stabilizer, preferably of sucrose, sucrose and mannitol, or sucrose and proline, in combination with the apolipoprotein: lipid ratio, the lyophilisation yields in a stable powder having a long shelf life. This powder may be stored, used directly or after storage as a powder or used after rehydration to form the reconstituted high density lipoprotein formulation.

The invention may be used for large scale production of reconstituted high density lipoprotein. The lyophilized product may be prepared for bulk preparations, or alternatively, the mixed protein/lipid solution may be apportioned in smaller containers (for example, single dose units) prior to lyophilization, and such smaller units may be used as sterile unit dosage forms. The lyophilized formulation can be reconstituted in order to obtain a solution or suspension of the protein-lipid complex, that is the reconstituted high density lipoprotein. The lyophilized powder is rehydrated with an aqueous solution to a suitable volume. Preferred aqueous solutions are water for injection (WFI), phosphate-buffer saline or a physiological saline solution. The mixture can be agitated to facilitate rehydration. Preferably, the reconstitution step is conducted at room temperature.

It is well known to the person skilled in the art how to obtain a solution comprising the lipid, and the apolipoprotein, such as described in WO 2012/000048.

In one preferred embodiment, the invention provides a method of producing a rHDL formulation including the step of adding the lyophilization stabilizer to the solution comprising the lipid, and the apolipoprotein until a concentration of from about 1.0% to about 6.0% (w/w of rHDL formulation) is reached, e.g. from 1.0, 1.1, 1.2 or 1.3 to 5.5, 5.6, 5.7, 5.8, 5.9, or 6.0. In a preferred embodiment, the lyophilization stabilizer is added until a concentration from about 1.0% to less than 6.0% e.g. from about 1.0% to 5.9% is reached. Preferably lyophilization stabilizer is added until a concentration from about 3.0 to less than 6.0%, e.g. from about 3.0 to 5.9% is reached. More preferably the lyophilization stabilizer is added until a concentration from about 4.0 to 5.5%, particularly 4.3 to 5.3%, more particularly 4.3 to 5.0%, and most preferably 4.6 to 4.8% (w/w) is reached. The solution may already contain stabilizer.

In preferred embodiments the solution additionally includes a detergent such as sodium cholate. In a preferred embodiment the rHDL formulation is manufactured by combining Apo A-I purified from plasma, with phosphatidylcholine (PC) in the presence of sodium cholate and sucrose at a concentration from about 1.0% to about 6.0%, preferably from about 1.0% to less than 6.0% w/w to produce disc shaped, non-covalently associated particles (MW approximately 144 kDa).

In particular embodiments the rHDL formulation is comprised of an Apo A-I (recombinant or purified from plasma) and phosphatidylcholine stabilized by cholate and sucrose at a concentration from about 1.0% to about 6.0% w/w, preferably from about 1.0% to less than 6.0%. Preferably the recombinant Apo A-I comprises either a wild type sequence or the Milano sequence (which when expressed forms dimers).

The lyophilized rHDL formulation of the present invention may be formed using any method of lyophilization known in the art, including, but not limited to, freeze drying, i.e. the apolipoprotein/lipid-containing solution is subjected to freezing followed by reduced pressure evaporation.

The lyophilized rHDL formulations that are provided can retain substantially their original stability characteristics for at least 2, 4, 6, 8, 10, 12, 18, 24, 36 or more months. For example, lyophilized rHDL formulations stored at 2-8° C. or 25° C. can typically retain substantially the same molecular size distribution as measured by HPLC-SEC when stored for 6 months or longer. Particular embodiments of the rHDL formulation can be stable and suitable for commercial pharmaceutical use for at least 6 months, 12 months, 18 months, 24 months, 36 months or even longer when stored at 2-8° C. and/or room temperature.

The rHDL formulation according to the present invention may be used in treating a disease, disorder or condition in a human. Suitably, the disease, disorder or condition is responsive to prophylactic or therapeutic administration of the rHDL formulation according to the present invention. Examples of such diseases, disorders or conditions include atherosclerosis; cardiovascular disease (e.g. acute coronary syndrome (ACS) such as angina pectoris and myocardial infarction); or diseases, disorders or conditions such as diabetes that predispose to ACS; hypercholesterolaemia (e.g. elevated serum cholesterol or elevated LDL cholesterol) and hypocholesterolaemia resulting from reduced levels of high-density lipoprotein (HDL), such as being symptomatic of Tangier disease.

rHDL formulations according to the present invention may be administered by any route of administration known in the art. Preferably, rHDL formulations are administered parenterally, such as by intravenous (IV) infusion or injection. In preferred embodiments the rHDL formulation comprises Apo A-I (recombinant or purified from plasma) which has been reconstituted to form particles suitable for IV infusion.

The administered dosage of the rHDL formulation may be in the range of from about 1 to about 120 mg/kg body weight. Preferably, the dosage is in the range of from about 5 to about 80 mg/kg inclusive of 8 mg/kg, 10 mg/kg, 12 mg/kg, 20 mg/kg, 30 mg/kg, 40 mg/kg, 50 mg/kg, 60 mg/kg, and 70 mg/kg dosages. Alternatively delivery can be achieved by fixed dosages of rHDL, that is, in an amount independent of patient body weight. Preferred fixed dosages include 0.1-15 g, 0.5-12 g, 1-10 g, 2-9 g, 3-8 g, 4-7 g or 5-6 g of apolipoprotein. Particularly preferred fixed dosages include 1-2 g, 3-4 g, 5-6 g or 6-7 g of apolipoprotein. Non-limiting examples of specific fixed dosages include 0.25 g, 0.5 g, 1.0 g, 1.7 g, 2.0 g, 3.4 g, 4.0 g, 5.1 g, 6.0 g, 6.8 g and 8.0 g of apolipoprotein. Accordingly, a vial preferably comprises the lyophilized rHDL formulation with a protein content of 0.25 g, 0.5 g, 1, 2, 2.5, 3, 3.5, 4, 4.5, 5, 5.5, 6, 6.5, 7, 8 or 10 g per vial. More preferably the protein content is either 0.5, 1, 2, 4, 6, 8, or 10 g per vial.

The invention also provides an apolipoprotein kit comprising one or more unit doses of the apolipoprotein formulation disclosed herein and one or more other kit components.

Suitably, the kit is for prophylactically or therapeutically treating a disease, disorder or condition in a human, as hereinbefore described.

Non-limiting examples of one or more other kit components include instructions for use; vials, containers or other storage vessels containing each of the unit doses; delivery devices such as needles, catheters, syringes, tubing and the like; and/or packaging suitable for safely and conveniently storing and/or transporting the kit. Preferably the instructions for use are a label or package insert, wherein the label or package insert indicates that the apolipoprotein formulation may be used to treat a disease or condition such as cardiovascular disease by administering a fixed dose amount to a human subject in need thereof.

A 'package insert' refers to instructions included in commercial packages of the apolipoprotein formulations, that contains information about the indications, usage, dosage, administration, contraindications and/or warnings concerning the use of such apolipoprotein formations.

For the purposes herein, a 'vial' refers to a container which holds an apolipoprotein formulation. The vial may be sealed by a stopper pierceable by a syringe. Generally, the vial is formed from a glass material. The apolipoprotein formulation in the vial can be in various states including liquid, lyophilized, frozen etc. The fixed dosage apolipoprotein formulation is preferably stable as turbidity is a preferred measure. A turbidity level of below about 5, 10, 15, 20, or 30 NTU can generally be considered a stable dosage apolipoprotein formulation. Turbidity measurements can be taken by incubating the apolipoprotein formulations over time periods such as 0 hr, 2 hr, 4 hr, 6 hr, 12 hr, 18 hr, 24 hr, 36 hr, 72 hr, 7 days and 14 days at storage temperatures such as room temperature or 2 to 8° C. Preferably the apolipoprotein formulation is considered to be stable as a liquid when it is stored for 14 days at room temperature and exhibits a turbidity of less than about 15 NTU.

The kit may facilitate administration of the apolipoprotein formulation by a health professional or self-administration by a patient or caregiver.

As used herein, the term "comprising" encompasses "including" as well as "consisting" e.g. a formulation or a component of a formulation that is described as "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

Where the invention provides a process involving multiple sequential steps, the invention can also provide a process involving less than the total number of steps. The different steps can be performed at very different times by different people in different places (e.g. in different countries).

Unless specifically stated, a process comprising a step of mixing two or more components does not require any specific order of mixing. Thus components can be mixed in any order. Where there are three components then two components can be combined with each other, and then the combination may be combined with the third component, etc.

Various embodiments of the invention are described herein. It will be appreciated that the features specified in each embodiment may be combined with other specified features, to provide further embodiments. In particular, embodiments highlighted herein as being suitable, typical or preferred may be combined with each other (except when they are mutually exclusive).

EXAMPLES

Example 1

Preparation of the Samples

To make the samples for the following experiments, sodium cholate (New Zealand Pharmaceuticals) was dissolved in buffer (10 mM NaCl, 1 mM EDTA, 10 mM TRIS, pH 8.0) and stirred until clear. Soybean phosphatidylcholine (Phospholipid GmbH) was added to an appropriate volume of the cholate and stirred for 16 h at room temperature. The Apo A-I solution was diluted to a protein concentration of 9.0 mg/mL (determined by OD280) with 10 mM NaCl and mixed with an appropriate volume of the lipid solution to obtain protein to lipid ratio in the range of 1:45 to 1:65. The mixture was stirred at 2-8° C. for 30 min to 16 h. The HDL mimetics were prepared by cholate dialysis using 1% sucrose as a diafiltration buffer. The eluate was concentrated to a protein concentration of 33 to 38 g protein/L. Sucrose was added to obtain the desired concentration (1%, 2%, 3%, 4%, 5%, 6.5%, 7%, 10% w/w). The pH of the solution was adjusted, with 0.2 M NaOH to pH 7.50±0.1 after which WFI (water for injection) was added to obtain a protein concentration of 30 mg/mL. The final formulations were then sterile filtered through a 0.2+0.1 μm filter and filled into 100 mL glass vials at 1.7 g protein per vial and lyophilized.

In some formulations proline was added to the desired concentration. Proline maintains an isotonic formulation.

Example 2

Molecular Size Distribution

Figure 1:
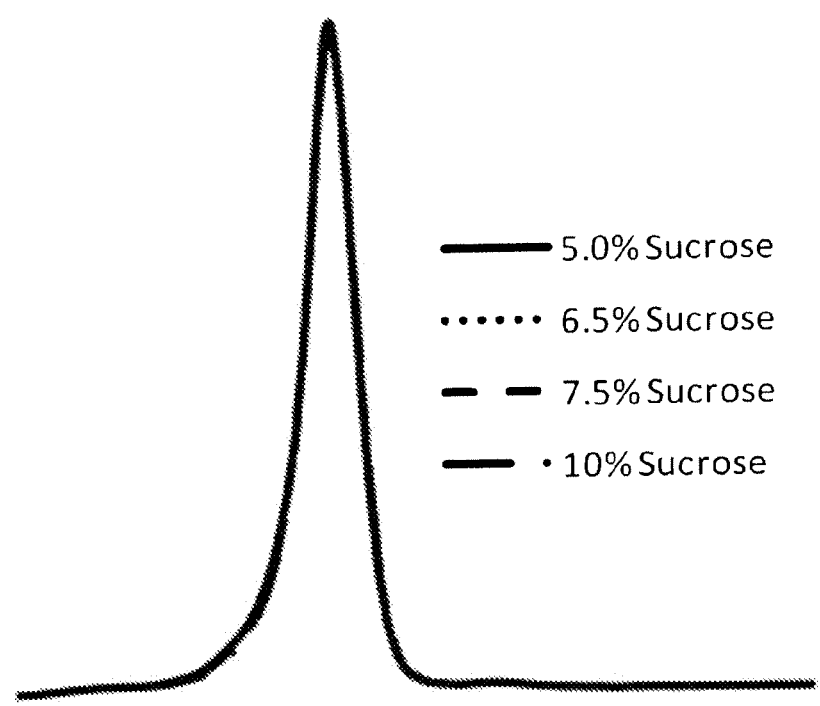
FIG. 1: Molecular size distribution of formulations containing 5 to 10% w/w sucrose.

Particle formation was determined using HPLC-SEC and assessed by the molecular size distribution of the various formulations. Little difference was observed for formulations containing 5-10% w/w sucrose in the final formulation (FIG. 1), indicating that formulations containing ≥5% w/w sucrose did not affect particle stability after reconstitution. FIG. 1 shows a complete chromatogram of (1) internal control, 2: 5% w/w sucrose, 3: 6.5% w/w sucrose, 4: 7.5% w/w sucrose and 5: 10% w/w sucrose.

Figure 2A:
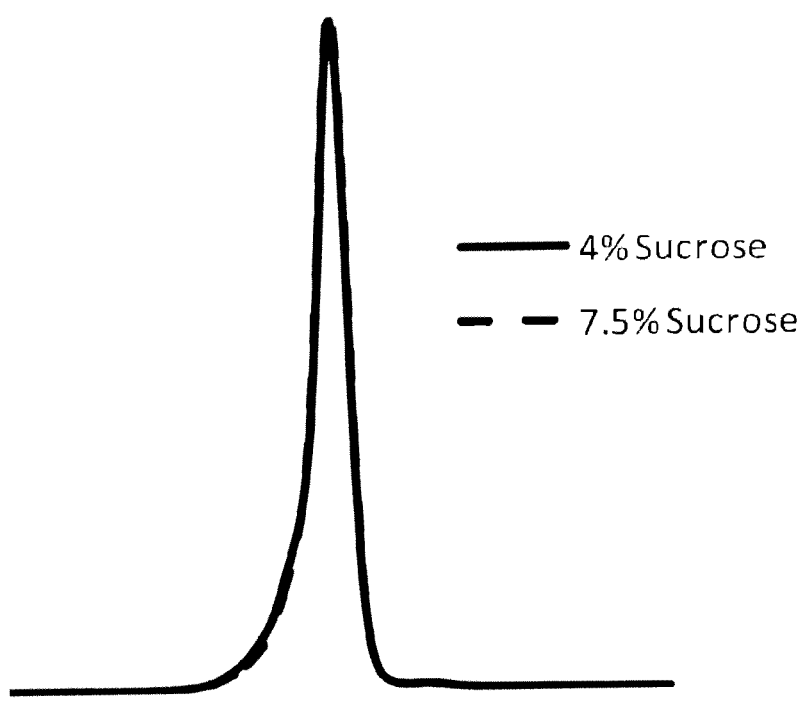
FIG. 2A: Direct comparison of molecular size distribution of formulations containing 4 and 7.5% w/w sucrose.

In addition a direct comparison between a 7.5% w/w sucrose formulation and 4% w/w sucrose formulation demonstrated that these formulations exhibit a similar molecular size distribution (FIG. 2A).

Figure 2B:
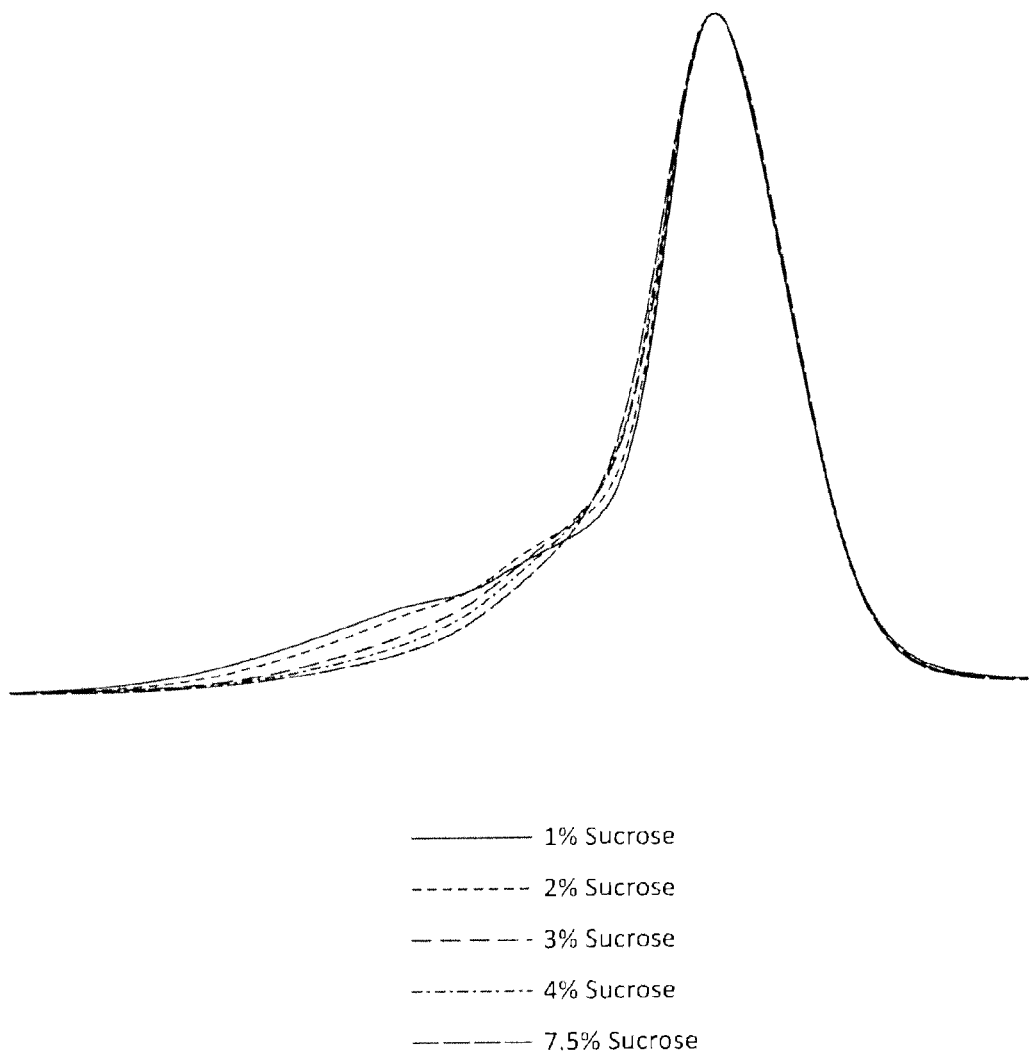
FIG. 2B: Molecular size distribution of formulations containing 1, 2, 3, 4 and 7.5% (w/w) sucrose.
Figure 2C:
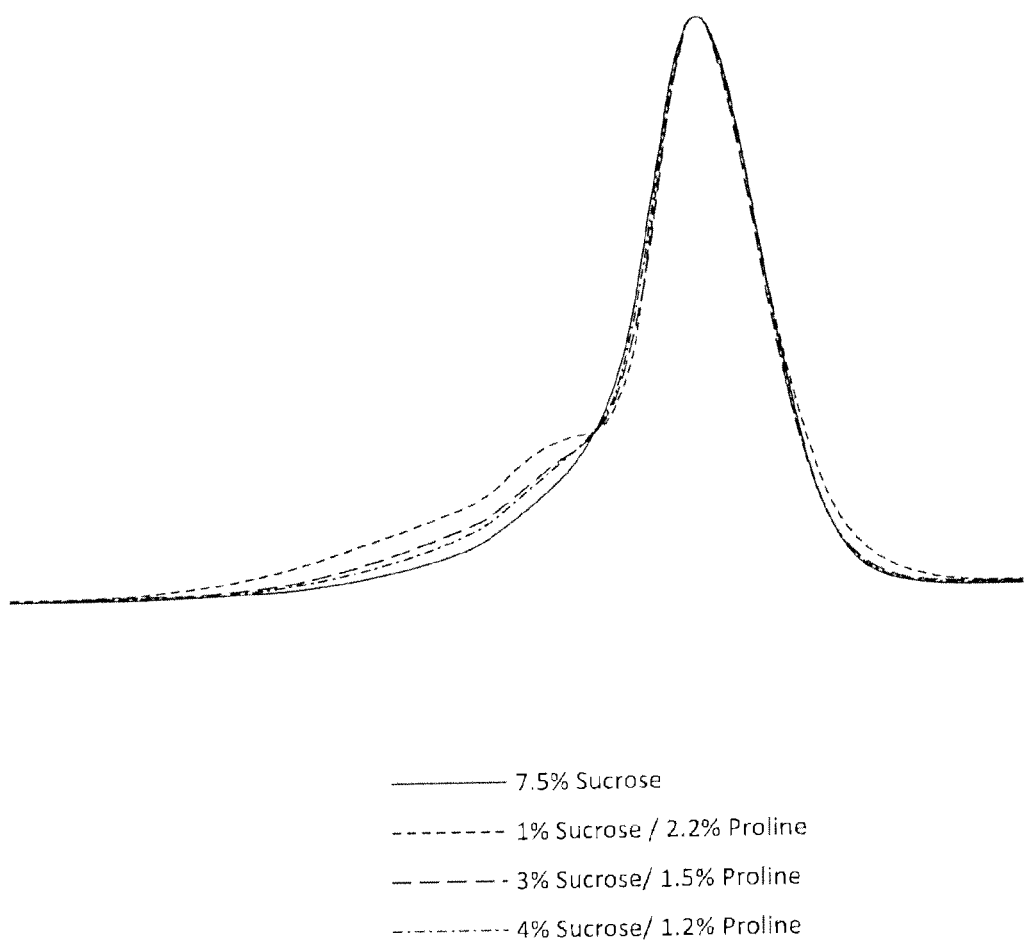
FIG. 2C: Molecular size distribution of formulations containing sucrose and proline and 7.5% sucrose.

FIGS. 2B and 2C show the results for sucrose concentrations 1, 2, 3, and 4% (w/w) and formulations comprising sucrose and proline.

All tested formulations are stable. The sucrose content of 4 to 7.5% w/w was optimum and did not affect the particle stability after reconstitution.

Example 3

LCAT Activation

A measure of the effectiveness of the rHDL particles in various formulations was determined by measuring the LCAT activity. HDL particles are capable of sequestering cholesterol from plaques formed along artery walls or cells by interaction with the ATP-binding cassette transporter A1 (ABCA1). Lecithin-cholesterol acyltransferase (LCAT), a plasma enzyme converts the free cholesterol into cholesteryl ester (a more hydrophobic form of cholesterol), which is then sequestered into the core of the HDL particle before being transported to the liver to be metabolized. If the sucrose content in the final formulation affected the efficacy of the rHDL particle, LCAT activity would decrease.

Figure 3A:
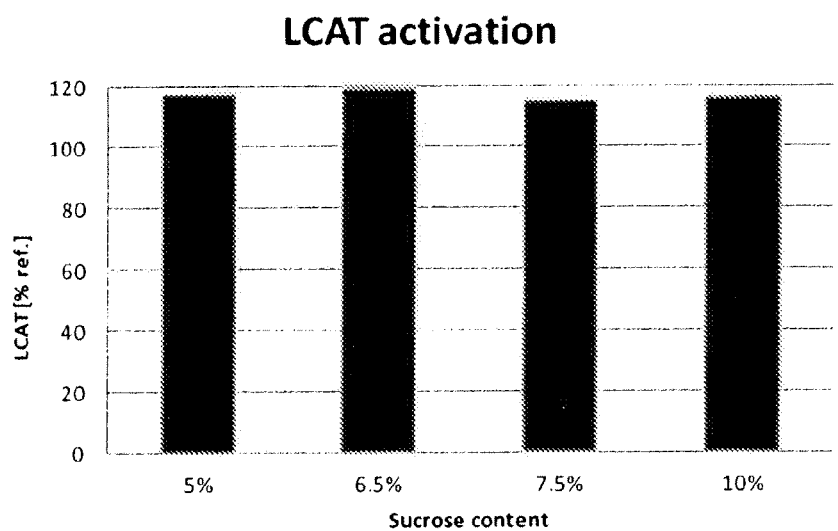
FIGS. 3A and 3B: LCAT activity for 4 to 10% w/w sucrose formulations.
Figure 3B:
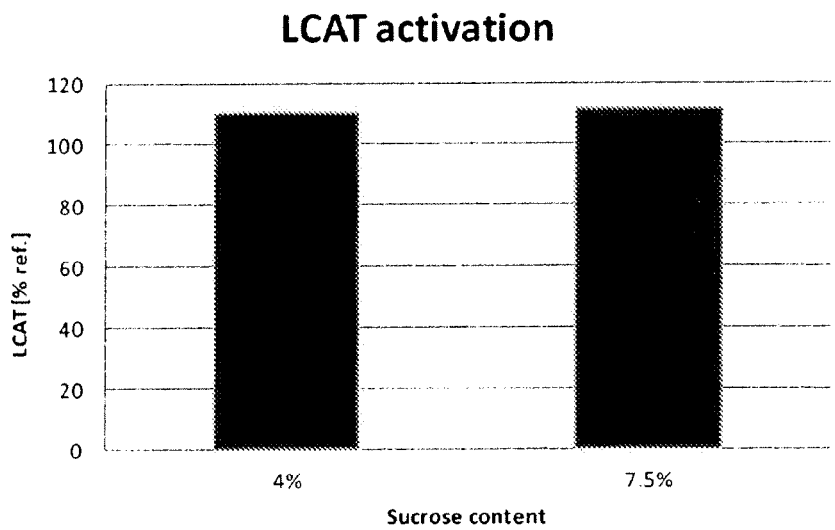
Figure 3C:
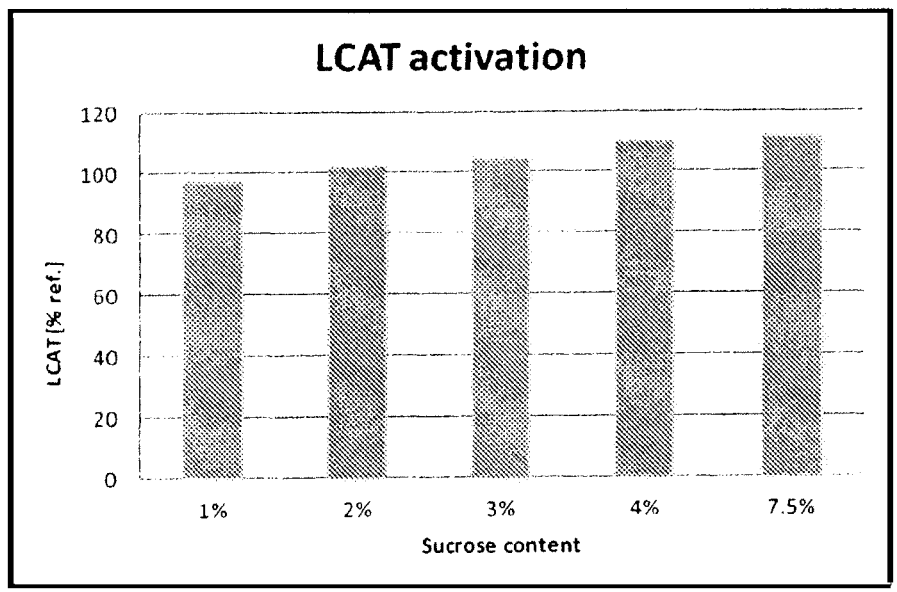
FIG. 3C: LCAT activity for 1, 2, 3, 4 and 7.5% w/w sucrose formulations.
Figure 3D:
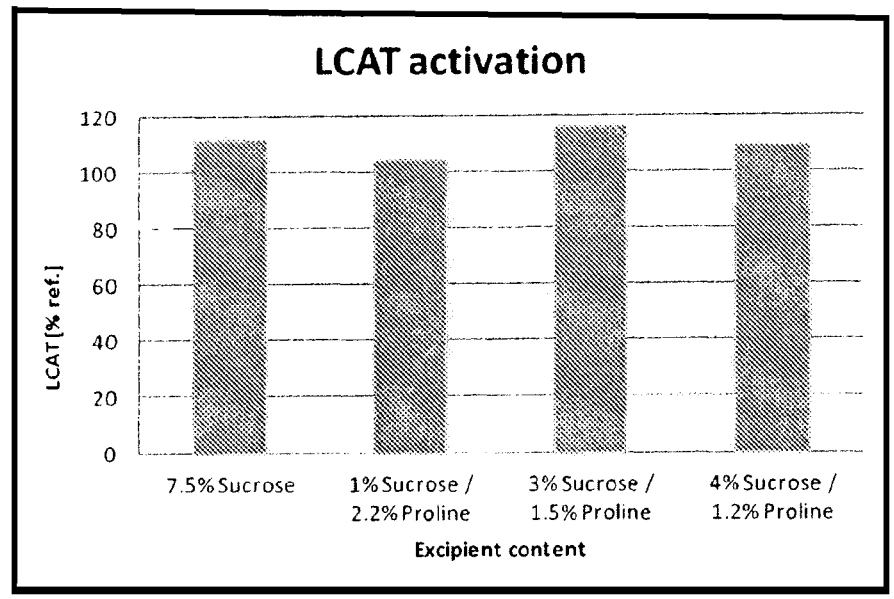
FIG. 3D: LCAT activity for formulations containing sucrose and proline.

FIGS. 3A and 3B show LCAT activity for 4-10% w/w sucrose formulations. FIG. 3C shows LCAT activity for 1-4% w/w sucrose formulations. Very little difference is seen in LCAT activity when the sucrose ranges from 5-10% w/w in the final formulation (FIG. 3A), however a slight decreasing trend is evident when the sucrose is further reduced to 4% w/w (FIG. 3B). FIG. 3D shows LCAT activity for formulations comprising sucrose and proline. No apparent trend in LCAT activity is observed for formulations containing sucrose and proline. Thus the efficacy of the HDL particle in sucrose/proline formulations is maintained.

Example 4

Cholesterol Efflux

Reverse cholesterol transport (RCT) is a pathway by which accumulated cholesterol is transported from the vessel wall to the liver for excretion. Cells efflux free cholesterol to lipid-poor Apo A-I via the ABCA1 pathway. The cholesterol efflux assay measures the capacity of HDL to accept cholesterol released from cells. It is anticipated that if sucrose content affected particle formation and/or integrity, differences would affect cholesterol efflux.

Figure 4A:
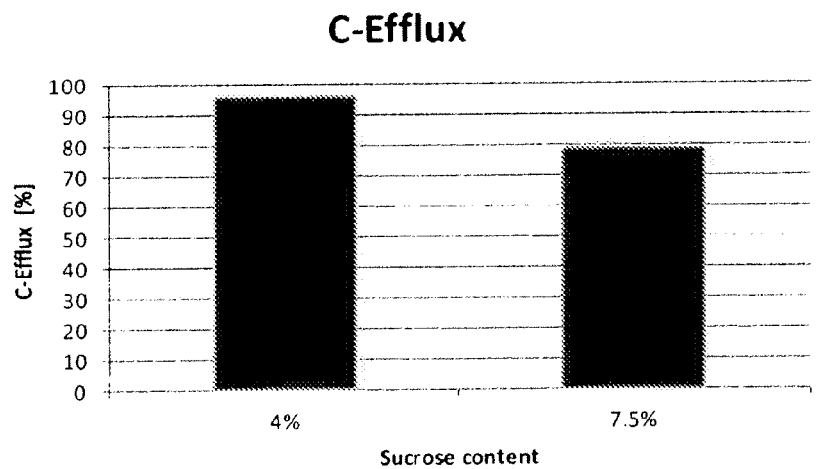
FIG. 4A to 4B: Impact of sucrose concentration on cholesterol efflux.
Figure 4B:
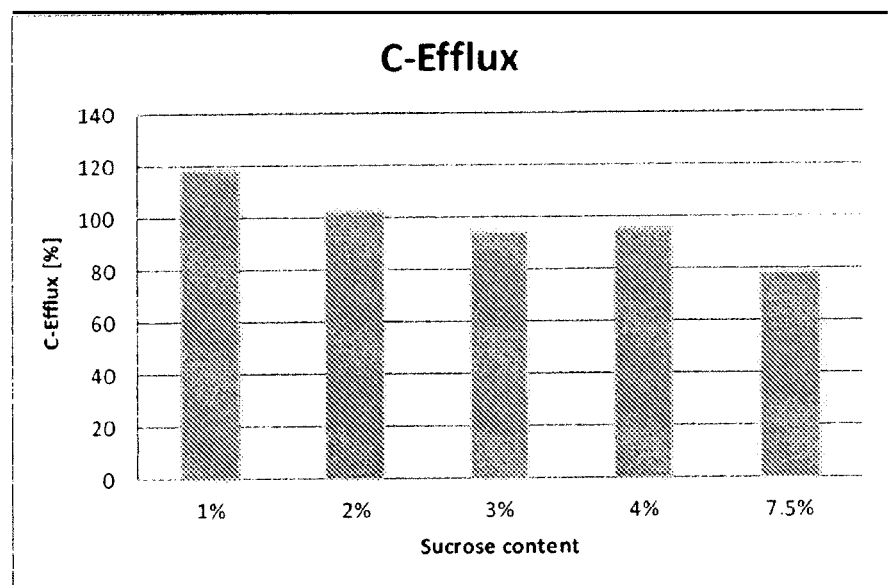
Figure 4C:
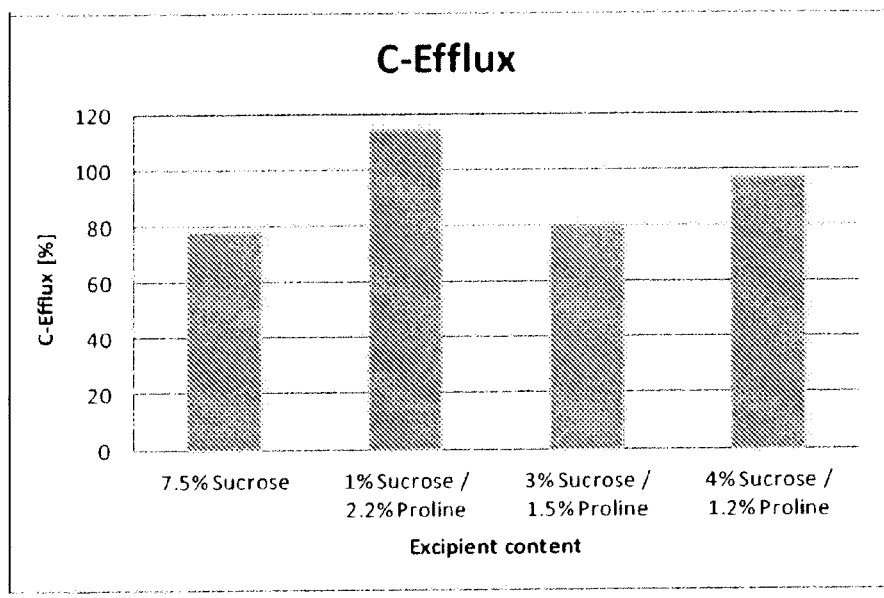
FIG. 4C: Impact of formulations containing sucrose and proline on cholesterol efflux.

FIGS. 4A and 4B show that as sucrose concentration decreases from 7.5% w/w to 4% w/w the cholesterol efflux increased. No apparent difference in cholesterol efflux was observed between the proline containing formulations and the 7.5% sucrose formulation (FIG. 4C).

Example 5

Turbidity

The term turbidity is used to describe the cloudiness or haze in a solution. Strictly, turbidity arises from the multiple scattering events of visible light by elements present in the solution. Since turbidity arises from the net scattered light, it depends on the sample path length, protein concentration and size of the protein/aggregates/particles. Given that all reduced sucrose formulations contained the same protein concentration upon reconstitution and were measured with the same path length, differences in turbidity can be attributed to differences in the size and/or number of protein/aggregates/particles resulting from the various sucrose formulations.

Figure 5A:
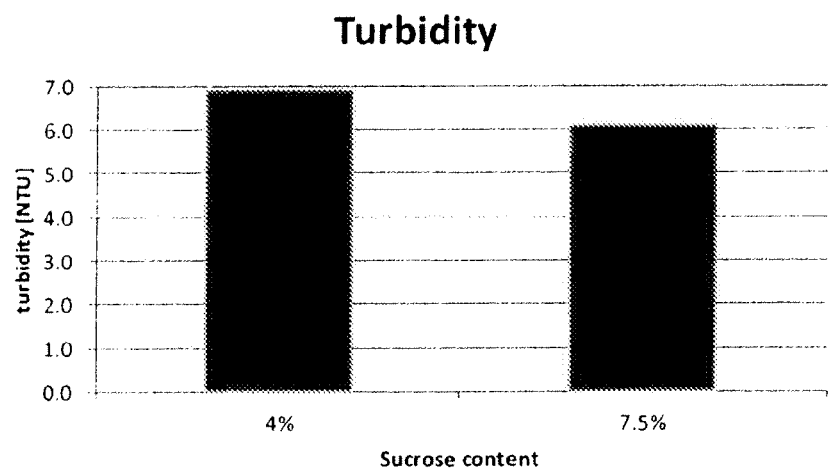
FIGS. 5A to 5H: Turbidity of formulations with different sucrose concentrations and formulations containing sucrose and proline.
Figure 5B:
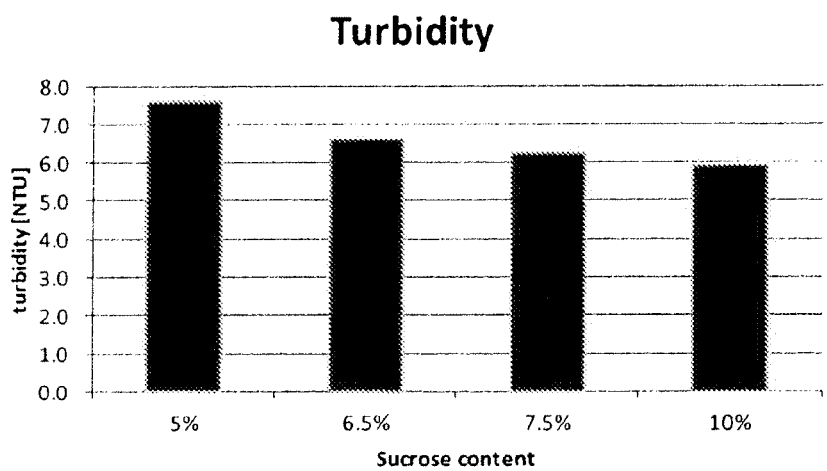
Figure 5C:
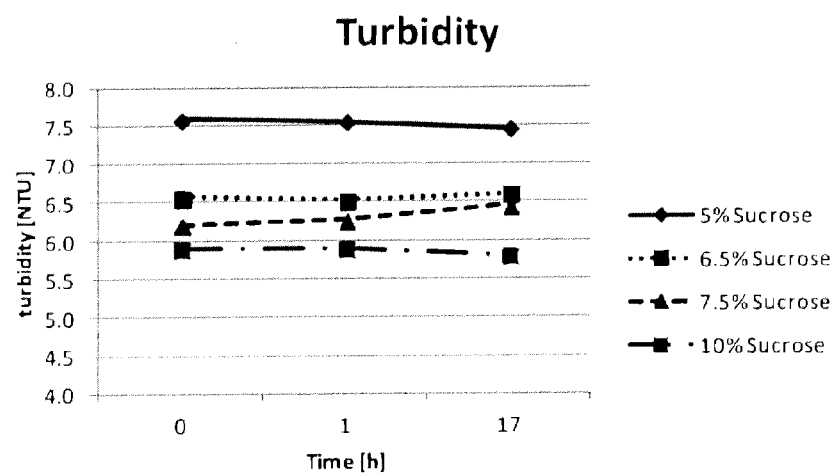
Figure 5D:
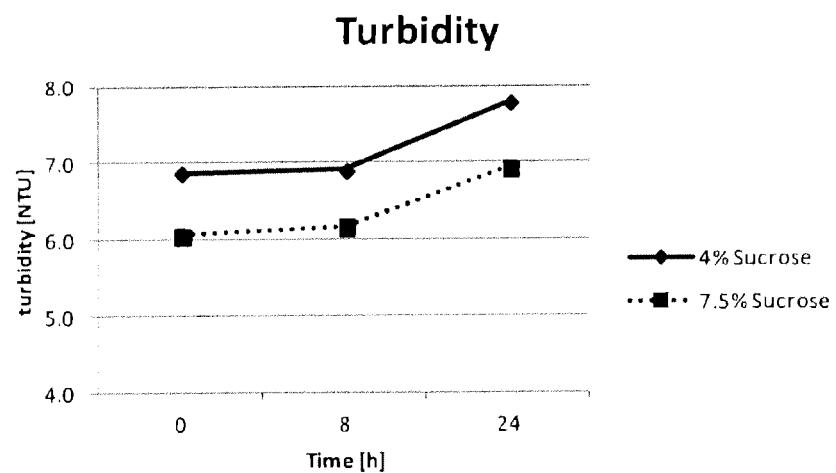
Figure 5E:
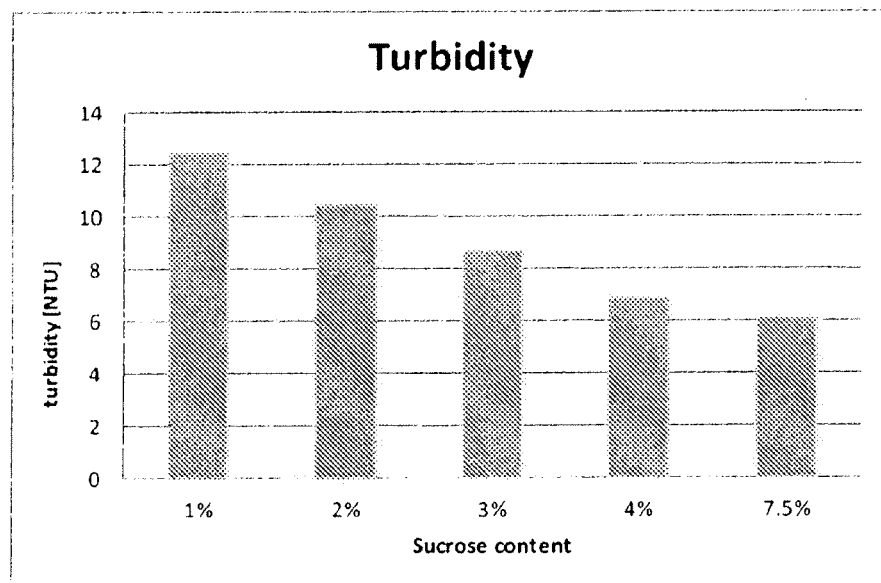
Figure 5F:
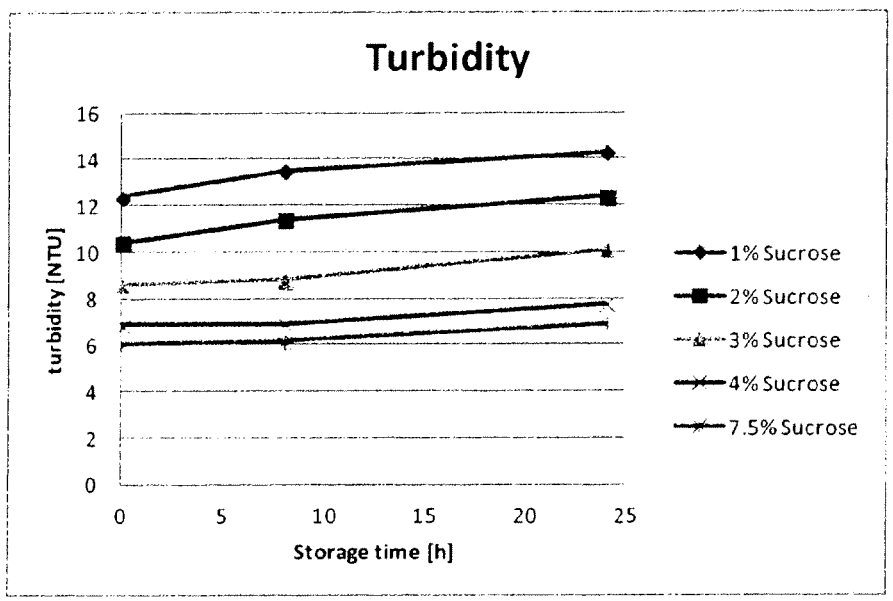
Figure 5G:
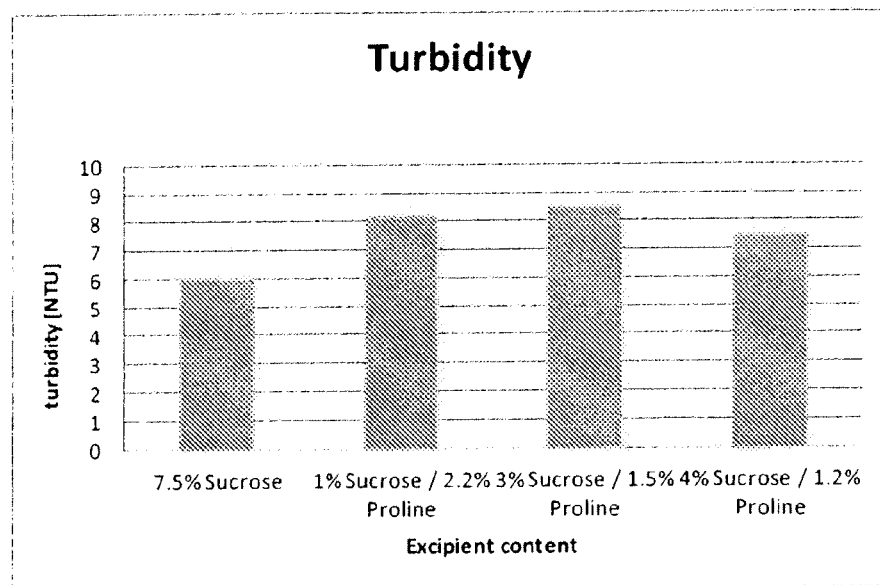
Figure 5H:
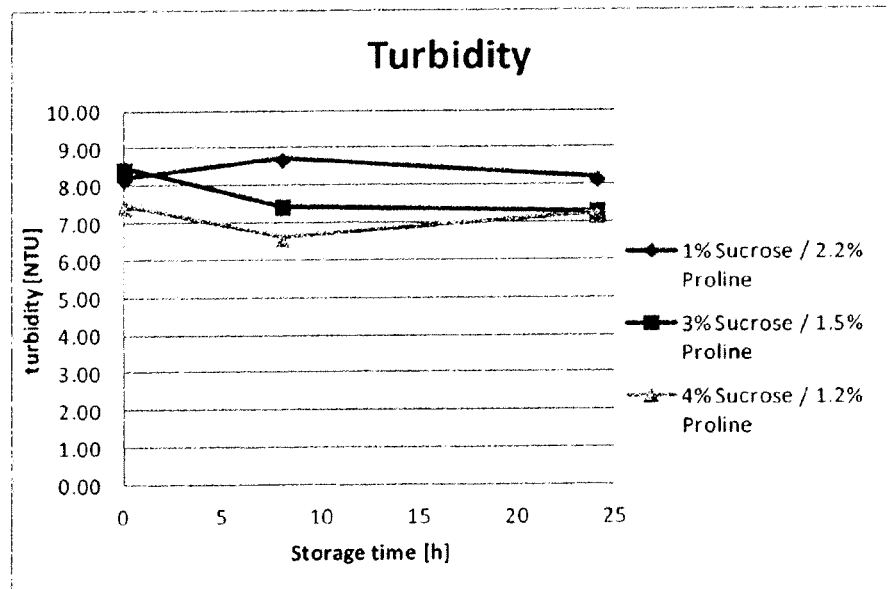

Formulations containing 4-10% w/w sucrose produced similar turbid solutions upon reconstitution (FIGS. 5A & 5B). Sucrose concentrations of less than 4% showed increased turbidity (FIGS. 5E and 5G). Based on turbidity, sucrose concentrations of 4% (w/w) and above are optimum.

Relative increases in the turbidity of a solution upon storage, is often cited as an indication of aggregation in protein biopharmaceuticals. FIGS. 5C, 5D, 5F and 5H show that little to no increase in turbidity are seen upon storage in liquid form, thereby indicating stability of the particles.

Example 6

Lyo Cake Appearance

Figure 6:
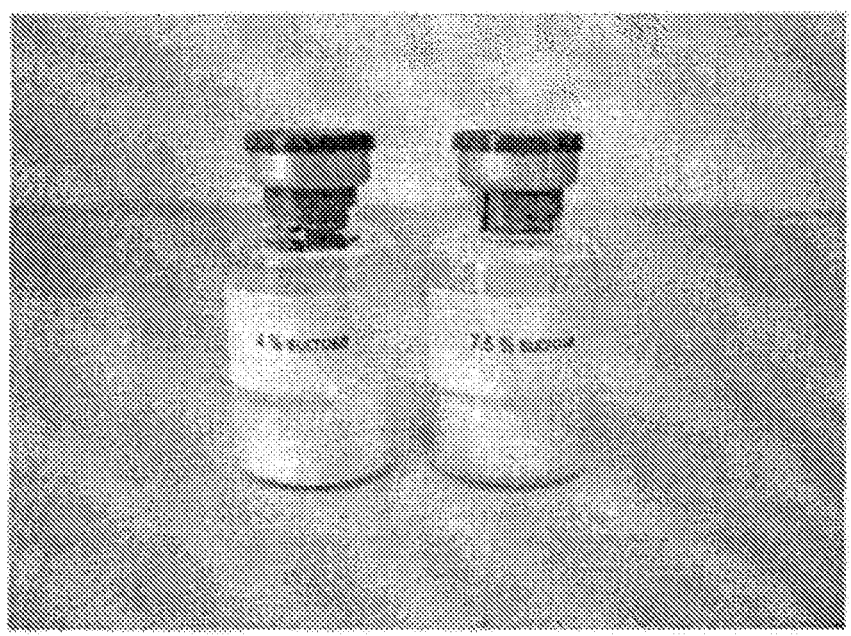
FIG. 6: Picture of lyo cakes with different sucrose concentration.

Sucrose formulations with 4% w/w and 7.5% w/w sucrose produced the most stable lyo cakes (FIG. 6).

Figure 7:
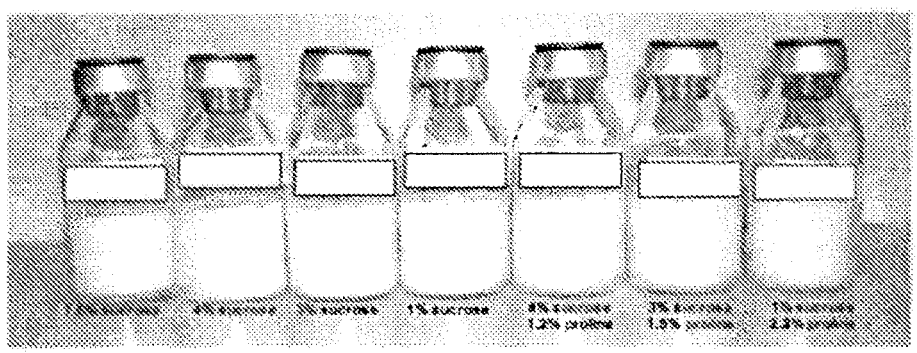
FIG. 7: Picture of lyo cakes with different sucrose concentrations and sucrose and proline.

Sucrose formulations with 1 to 4% w/w, and formulations containing sucrose and proline, also produced stable lyo cakes (FIG. 7).

The invention claimed is:

1. A reconstituted high density lipoprotein (rHDL) formulation comprising an apolipoprotein, a lipid, and a lyophilization stabilizer, wherein the ratio between the apolipoprotein and the lipid is from about 1:20 to about 1:120 (mol:mol) and the lyophilization stabilizer comprises sucrose present in a concentration of from about 1.0% to less than 6.0% w/w of the rHDL formulation, and wherein the lyophilization stabilizer is present in a total concentration of from about 1.0% to less than 6.0% w/w of the rHDL formulation.

2. The rHDL formulation according to claim 1, wherein the ratio between the apolipoprotein and the lyophilization stabilizer is from about 1:1 to about 1:3 (w:w).

3. The rHDL formulation according to claim 1, wherein the lyophilization stabilizer is present in a concentration from about 4.0 to 5.5% (w/w).

4. The rHDL formulation according to claim 1, wherein the formulation further comprises a detergent.

5. The rHDL formulation according to claim 4, wherein the detergent comprises sodium cholate.

6. The rHDL formulation according to claim 1, wherein the ratio between the apolipoprotein and the lipid is from about 1:20 to about 1:100 (mol:mol).

7. The rHDL formulation according to claim 1, wherein the concentration of the apolipoprotein is from about 5 to about 50 mg/ml.

8. The rHDL formulation according to claim 1, wherein the apolipoprotein comprises apolipoprotein A-I (Apo A-I).

9. The rHDL formulation according to claim 8, wherein the Apo A-I is selected from the group consisting of Apo A-I purified from plasma and recombinant Apo A-I.

10. The rHDL formulation according to claim 9, wherein the Apo A-I comprises the wild type or Milano Apo A-I sequence.

11. The rHDL formulation according to claim 1, wherein the lipid comprises at least one charged or non-charged phospholipid or a mixture thereof.

12. The rHDL formulation according to claim 11, wherein the lipid comprises a phosphatidylcholine.

13. The rHDL formulation according to claim 1, wherein the apolipoprotein is Apo A-I purified from plasma, the lipid is phosphatidylcholine, the lyophilization stabilizer is sucrose and the formulation further comprises sodium cholate detergent.

14. The rHDL formulation according to claim 13, wherein the ratio between the apolipoprotein and the lipid is from 1:45 to 1:65 (mol:mol); the lyophilization stabilizer is present in a concentration of 4.6 to 4.8% (w/w); and the sodium cholate is present at a concentration of 0.5 to 1.5 mg/mL.

15. The rHDL, formulation according to claim 1, wherein the formulation has a pH in the range of 6 to 8.

16. The rHDL formulation according to claim 1, wherein the formulation is lyophilized.

17. A method of producing a rHDL formulation comprising combining an apolipoprotein, a lipid, and a lyophilization stabilizer comprising sucrose such that the ratio between the apolipoprotein and the lipid is from 1:20 to 1:120 (mol:mol), and the sucrose is present at a concentration of from about 1.0% to less than 6.0% (w/w) of the formulation, and wherein the lyophilization stabilizer is present in a total concentration of from about 1.0% to less than 6.0% w/w of the rHDL formulation.

18. A method of treating a disease, disorder or condition in a human in need thereof selected from the group consisting of cardiovascular disease, hypercholesterolaemia and hypocholesterolaemia, comprising administering to said human an rHDL formulation according to claim 1.

19. The method according to claim 18, wherein the disease, disorder or condition is selected from the group consisting of acute coronary syndrome (ACS), atherosclerosis, angina pectoris and myocardial infarction.

20. The rHDL formulation according to claim 1, wherein the formulation is suitable for parenteral administration.

21. The rHDL formulation according to claim 1, wherein the formulation is suitable for intravenous administration.

22. The rHDL formulation according to claim 1, wherein the ratio between the apolipoprotein and the lyophilization stabilizer is from about 1:1 to about 1:2.4 (w:w).

23. The rHDL formulation according to claim 21, wherein the ratio between the apolipoprotein and the lyophilization stabilizer is from about 1:1 to less than 1:2 (w:w).

24. The rHDL formulation according to claim 1, wherein the lyophilization stabilizer is present in a concentration from 4.3 to 5.3% (w/w).

25. The rHDL formulation according to claim 23, wherein the lyophilization stabilizer is present in a concentration from 4.6 to 4.8% (w/w).

* * * * *